(12) United States Patent
Manzer

(10) Patent No.: US 7,025,819 B2
(45) Date of Patent: Apr. 11, 2006

(54) PRODUCTION OF 5-METHYL-N-(METHYL ARYL)-2-PYRROLIDONE, 5-METHYL-N-(METHYL CYCLOALKYL)-2-PYRROLIDONE AND 5-METHYL-N-ALKYL-2-PYRROLIDONE BY REDUCTIVE AMINATION OF LEVULINIC ACID ESTERS WITH CYANO COMPOUNDS

(75) Inventor: Leo Ernest Manzer, Wilmington, DE (US)

(73) Assignee: E. I. duPont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/966,087

(22) Filed: Oct. 15, 2004

(65) Prior Publication Data

US 2005/0059829 A1 Mar. 17, 2005

Related U.S. Application Data

(62) Division of application No. 10/396,087, filed on Mar. 24, 2003, now Pat. No. 6,916,842.

(51) Int. Cl.
*C07D 11/02* (2006.01)
*C07D 207/12* (2006.01)
(52) U.S. Cl. .................................. 106/31.78; 548/517
(58) Field of Classification Search ................ 548/517
See application file for complete search history.

(56) References Cited

U.S. PATENT DOCUMENTS

| 3,235,562 A | 2/1966 | Shilling et al. |
| 3,337,585 A | 8/1967 | Swakon et al. |
| 6,841,520 B1 * | 1/2005 | Manzer ....................... 504/283 |

* cited by examiner

*Primary Examiner*—Kamal A. Saeed
(74) *Attorney, Agent, or Firm*—Gerald E. Deitch

(57) ABSTRACT

This invention relates to a process for producing 5-methyl-N-(methyl aryl)-2-pyrrolidone, 5-methyl-N-(methyl cycloalkyl)-2-pyrrolidone and 5-methyl-N-alkyl-2-pyrrolidone by reductive amination of levulinic acid esters with aryl or alkyl cyano compounds utilizing a metal catalyst, which is optionally supported.

1 Claim, No Drawings

PRODUCTION OF 5-METHYL-N-(METHYL ARYL)-2-PYRROLIDONE, 5-METHYL-N-(METHYL CYCLOALKYL)-2-PYRROLIDONE AND 5-METHYL-N-ALKYL-2-PYRROLIDONE BY REDUCTIVE AMINATION OF LEVULINIC ACID ESTERS WITH CYANO COMPOUNDS

CROSS REFERENCE TO RELATED APPLICATIONS

This application is a divisional of application Ser. No. 10/396,087, filed Mar. 24, 2003, now U.S. Pat. No. 6,916,842, which is pending.

FIELD OF THE INVENTION

This invention relates to a process for producing 5-methyl-N-(methyl aryl)-2-pyrrolidone, 5-methyl-N-(methyl cycloalkyl)-2-pyrrolidone and 5-methyl-N-alkyl-2-pyrrolidone by reductive amination of levulinic acid esters with aryl or alkyl cyano compounds utilizing a metal catalyst, which is optionally supported.

BACKGROUND OF THE INVENTION

Levulinic acid is a well-known product of hexose acid hydrolysis, and can be inexpensively obtained from cellulose feedstocks. Consequently, it is an attractive starting material in producing many useful 5-carbon compounds and their derivatives. For example, N-cyclohexyl-2-pyrrolidone is used as a solvent or intermediate in many industrial applications, including the electronics industry (photo-resist stripping solutions), industrial cleaners, oil/gas well maintenance, and fiber dyeing. N-[2-hydroxyethyl]-2-pyrrolidone is useful in industrial cleaning, printing inks, and gasoline and oil additives. N-octyl-2-pyrrolidone is useful, for example, in the manufacture of agricultural products, as a detergent and dispersant, in industrial and metal cleaners, in printing inks and in fiber dyeing.

U.S. Pat. No. 3,337,585 discloses a process for preparing 5-methyl-1-alkyl-2-pyrrolidone utilizing levulinic acid and a primary alkyl amine at a temperature of 50° C. to 350° C. under carbon monoxide at a pressure of 1.0 to 101 MPa. Alkyl esters may also be used as a reactant with a primary amine. Additional potential primary amines include alkylene diamines, aryl amines and cycloalkyl amines. Nitriles (alkyl cyano compounds) are not used. U.S. Pat. No. 3,235,562 describes a vapor phase process for producing lactams by the reductive amination of oxo carboxylic acids or oxo carboxylic acid esters. Volatile alkyl or aryl primary amines may be used; nitriles are not used.

An efficient and low cost process for the production of aryl, alkyl and cycloalkyl pyrrolidones would be advantageous.

SUMMARY OF THE INVENTION

The present invention is a novel, one-step process for converting levulinic acid esters and cyano compounds to aryl, alkyl and cycloalkyl pyrrolidones as set forth in greater detail below in the presence of catalysts. Specifically, the present invention relates to a process for preparing 5-methyl-N-(methyl aryl)-2-pyrrolidone (III), 5-methyl-N-(methyl cycloalkyl)-2-pyrrolidone (IV), or a mixture thereof, which comprises the step of contacting a levulinic acid ester (I) with an aryl cyano compound (II) in the presence of a catalyst and hydrogen gas;

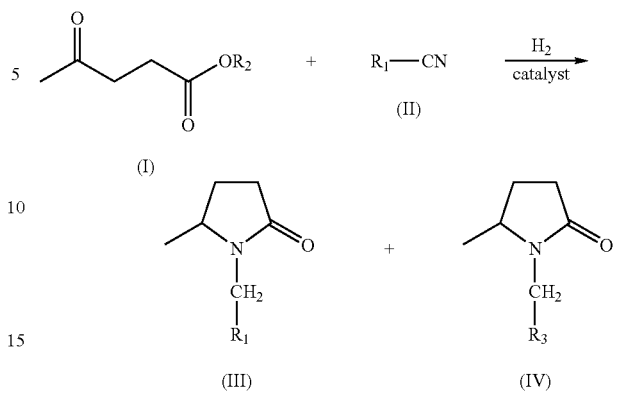

wherein $R_1$ is an aromatic group having from 6 to 30 carbons, $R_2$ is hydrocarbyl or substituted hydrocarbyl, $C_1$–$C_{18}$ unsubstituted or substituted alkyl, unsubstituted or substituted alkenyl, unsubstituted or substituted alkynyl, unsubstituted or substituted cycloalkyl, unsubstituted or substituted cycloalkyl containing at least one heteroatom, unsubstituted or substituted aryl, and unsubstituted or substituted heteroaryl, and $R_3$ is a fully or partially reduced derivative of $R_1$, and wherein 5-methyl-N-(methyl aryl)-2-pyrrolidone (III), 5-methyl-N-(methyl cycloalkyl)-2-pyrrolidone (IV), or a mixture thereof, may comprise 100% by weight of the total products formed, or wherein additional products may be produced.

The catalyst useful in the process of the invention is selected from metals from the group consisting of palladium, ruthenium, rhenium, rhodium, iridium, platinum, nickel, cobalt, copper, iron, osmium; compounds thereof; and combinations thereof.

The present invention also relates to a process for preparing 5-methyl-N-alkyl-2-pyrrolidone (VI) which comprises the step of contacting a levulinic acid ester (I) with an alkyl cyano compound (V) in the presence of a catalyst and hydrogen gas;

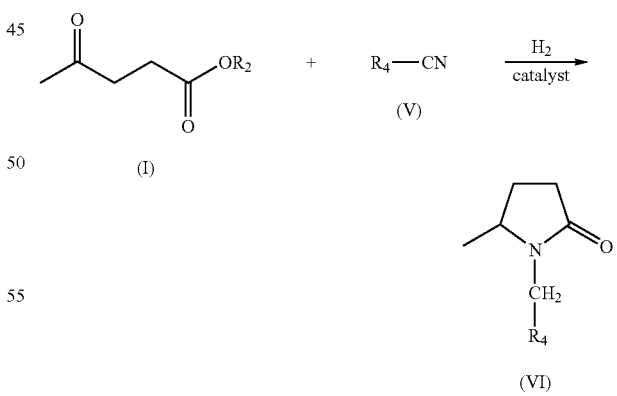

wherein $R_2$ is hydrocarbyl or substituted hydrocarbyl, $C_1$–$C_{18}$ unsubstituted or substituted alkyl, unsubstituted or substituted alkenyl, unsubstituted or substituted alkynyl, unsubstituted or substituted cycloalkyl, unsubstituted or substituted cycloalkyl containing at least one heteroatom, unsubstituted or substituted aryl, and unsubstituted or substituted heteroaryl, and wherein $R_4$ is an alkyl group having from 1 to 30 carbons, and wherein $R_4$ may be $C_1$–$C_{30}$ unsubstituted or substituted alkyl, $C_1$–$C_{30}$ unsubstituted or substituted alkenyl, $C_1$–$C_{30}$ unsubstituted or substituted alkynyl, $C_3$–$C_{30}$ unsubstituted or substituted cycloalkyl, or $C_3$–$C_{30}$ unsubstituted or substituted cycloalkyl containing at least one heteroatom, and wherein 5-methyl-N-alkyl-2-pyrrolidone (VI) may comprise 100% by weight of the total product formed, or wherein additional products may be produced.

The catalyst useful in this process of the invention is selected from metals from the group consisting of palladium, ruthenium, rhenium, rhodium, iridium, platinum, nickel, cobalt, copper, iron, osmium; compounds thereof; and combinations thereof.

DETAILED DESCRIPTION OF THE INVENTION

By "levulinic acid ester" is meant the compound having the following formula, wherein $R_2$ is hydrocarbyl or substituted hydrocarbyl, $C_1$–$C_{18}$ unsubstituted or substituted alkyl, unsubstituted or substituted alkenyl, unsubstituted or substituted alkynyl, unsubstituted or substituted cycloalkyl, unsubstituted or substituted cycloalkyl containing at least one heteroatom, unsubstituted or substituted aryl, and unsubstituted or substituted heteroaryl:

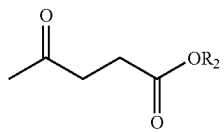

By "aryl cyano compound" is meant the compound having the formula R—CN wherein R is an aromatic group.

By "5-methyl-N-(methyl aryl)-2-pyrrolidone" is meant the compound having the general formula below wherein $R_1$ is an aryl group having from 6 to 30 carbons:

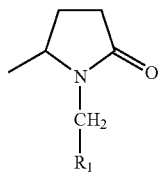

By "5-methyl-N-(methyl cycloalkyl)-2-pyrrolidone is meant the compound having the general formula below wherein $R_3$ is a cycloalkyl group having from 6 to 30 carbons:

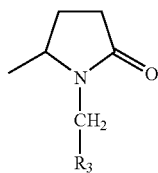

By "5-methyl-N-alkyl-2-pyrrolidone" is meant the compound having the general formula below wherein $R_4$ is $C_1$–$C_{30}$ unsubstituted or substituted alkyl, $C_1$–$C_{30}$ unsubstituted or substituted alkenyl, $C_1$–$C_{30}$ unsubstituted or substituted alkynyl, $C_3$–$C_{30}$ unsubstituted or substituted cycloalkyl, or $C_3$–$C_{30}$ unsubstituted or substituted cycloalkyl containing at least one heteroatom:

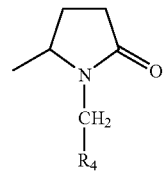

By "catalyst" is meant a substance that affects the rate of the reaction but not the reaction equilibrium, and emerges from the process chemically unchanged.

By "metal catalyst" is meant a catalyst that is comprised of at least one metal, at least one Raney metal, compounds thereof or combinations thereof.

By "promoter" is meant an element of the Periodic Table that is added to enhance the physical or chemical function of the catalyst. The promoter can also be added to retard undesirable side reactions and/or affect the rate of the reaction.

By "metal promoter" is meant a metallic compound that is added to enhance the physical or chemical function of a catalyst. The metal promoter can also be added to retard undesirable side reactions and/or affect the rate of the reaction.

By "fully or partially reduced derivative" of an aryl compound is meant a compound that can be derived from the parent compound by saturating or reducing one or more of the unsaturated bonds in the aromatic ring. Unsaturated compounds are compounds that contain one or more carbon to carbon double or triple bonds. For example, a fully reduced derivative of a phenyl group is a cyclohexyl group.

This invention relates to the synthesis of 5-methyl-N-(methyl aryl)-2-pyrrolidone (III), 5-methyl-N-(methyl cycloalkyl)-2-pyrrolidone (IV), or a mixture thereof, from a reaction between a levulinic acid ester (I) and an aryl cyano compound (II) in the presence of a catalyst and hydrogen;

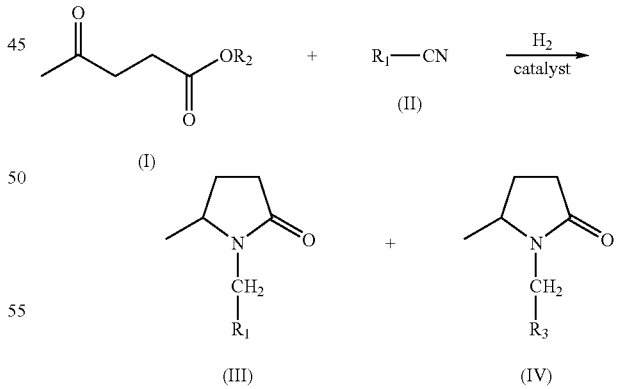

wherein $R_1$ is an aromatic group having from 6 to 30 carbons, $R_2$ is hydrocarbyl or substituted hydrocarbyl, $C_1$–$C_{18}$ unsubstituted or substituted alkyl, unsubstituted or substituted alkenyl, unsubstituted or substituted alkynyl, unsubstituted or substituted cycloalkyl, unsubstituted or substituted cycloalkyl containing at least one heteroatom, unsubstituted or substituted aryl, and unsubstituted or substituted heteroaryl, and $R_3$ is a fully or partially reduced derivative of $R_1$, and wherein 5-methyl-N-(methyl aryl)-2-pyrrolidone (III), 5-methyl-N-(methyl cycloalkyl)-2-pyrrolidone (IV), or a mixture thereof, may comprise 100% by weight of the total products formed, or wherein additional products may be produced.

In addition, this invention relates to the synthesis of 5-methyl-N-alkyl-2-pyrrolidone (VI) from a reaction between a levulinic acid ester (I) and an alkyl cyano (V) compound in the presence of a catalyst and hydrogen;

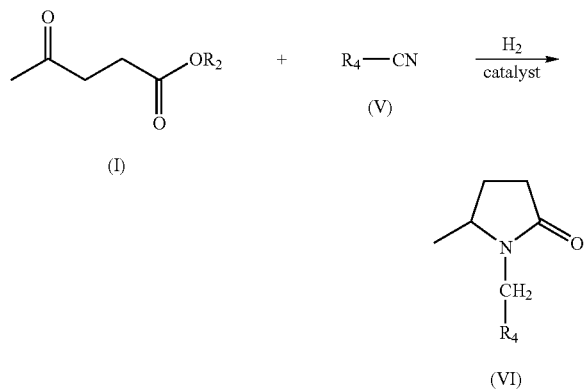

wherein $R_2$ is hydrocarbyl or substituted hydrocarbyl, $C_1$–$C_{18}$ unsubstituted or substituted alkyl, unsubstituted or substituted alkenyl, unsubstituted or substituted alkynyl, unsubstituted or substituted cycloalkyl, unsubstituted or substituted cycloalkyl containing at least one heteroatom, unsubstituted or substituted aryl, and unsubstituted or substituted heteroaryl, and wherein $R_4$ is an alkyl group having from 1 to 30 carbons, and wherein $R_4$ may be $C_1$–$C_{30}$ unsubstituted or substituted alkyl, $C_1$–$C_{30}$ unsubstituted or substituted alkenyl, $C_1$–$C_{30}$ unsubstituted or substituted alkynyl, $C_3$–$C_{30}$ unsubstituted or substituted cycloalkyl, or $C_3$–$C_{30}$ unsubstituted or substituted cycloalkyl containing at least one heteroatom, and wherein 5-methyl-N-alkyl-2-pyrrolidone (VI) may comprise 100% by weight of the total product formed, or wherein additional products may be produced.

A catalyst, with or without a support, may be present in the processes of the invention to effect the amination reactions. A promoter may optionally be used to aid the reactions. The promoter can be a metal.

The processes of the present invention may be carried out in batch, sequential batch (i.e., a series of batch reactors) or in continuous mode in any of the equipment customarily employed for continuous process (see for example, H. S. Fogler, Elementary Chemical Reaction Engineering, Prentice-Hall, Inc., N.J., USA). The condensate water formed as the product of the reaction is removed by separation methods customarily employed for such separations, such as distillation.

The aryl and cycloalkyl groups represented by $R_1$ and $R_3$ in Formulas (II), (III) and (IV) preferably have from 6 to 30 carbons. More preferably, the aryl and cycloalkyl groups represented by $R_1$ and $R_3$ in Formulas (II), (III) and (IV) have from 6 to 12 carbons. An example of a preferred embodiment of Formula (II) is benzonitrile; thus Formulas (III) and (IV) would be 5-methyl-N-benzyl-2-pyrrolidone and 5-methyl-N-(methyl cyclohexyl)-2-pyrrolidone, respectively. The hydrocarbyl or substituted hydrocarbyl group represented by $R_2$ preferably has from 1 to 18 carbons. More preferably, $R_2$ has from 1 to 12 carbons. The unsubstituted or substituted alkyl or cycloalkyl group represented by $R_4$ in Formulas (V) and (VI) preferably has from 1 to 30 carbons. More preferably the unsubstituted or substituted alkyl or cycloalkyl group represented by $R_4$ in Formulas (V) and (VI) has from 1 to 12 carbons.

In the processes of the invention, a molar ratio of cyano compound to levulinic acid ester of from about 0.01/1 to about 100/1 is preferred at the start of the reaction. A molar ratio of cyano compound to levulinic acid ester of from about 0.10/1 to about 5/1 is further preferred at the start of the reaction.

A temperature range of from about 25° C. to about 300° C. is preferred for the processes of the invention. A temperature range of from about 75° C. to about 225° C. is further preferred.

A pressure range of from about 0.3 MPa to about 20 MPa is employed for the processes of the invention. A pressure range of from about 1.3 MPa to about 7.6 MPa is preferred.

The reactions of the present invention can be performed in non-reacting solvent media such as water, alcohols, ethers, and pyrrolidones. Alternatively, the excess of aryl or alkyl cyano compound can also act as the solvent medium.

The catalyst useful in the invention is a substance that affects the rate of the reaction but not the reaction equilibrium, and emerges from the process chemically unchanged. A chemical promoter generally augments the activity of a catalyst. The promoter herein may be incorporated into the catalyst during any step in the chemical processing of the catalyst constituent. The chemical promoter generally enhances the physical or chemical function of the catalyst agent, but can also be added to retard undesirable side reactions.

The processes of the invention involve reductive amination of levulinic acid esters with aryl or alkyl cyano compounds, which is effected in the presence of a catalyst. The principal component of the catalyst useful herein is selected from metals from the group consisting of palladium, ruthenium, rhenium, rhodium, iridium, platinum, nickel, cobalt, copper, iron, osmium; compounds thereof; and combinations thereof.

A promoter may be used optionally in the reactions of the present invention. The promoter herein may be incorporated into the catalyst during any step in the chemical processing of the catalyst constituent. Suitable promoters for the processes of the invention include metals selected from tin, zinc, copper, gold, silver, and combinations thereof. The preferred metal promoter is tin. Other promoters that can be used are elements selected from Group 1 and Group 2 of the Periodic Table.

The catalyst used in the process may be supported or unsupported. A supported catalyst is one in which the active catalyst agent is deposited on a support material by a number of methods, such as spraying, soaking or physical mixing, followed by drying, calcination, and if necessary, activation through methods such as reduction or oxidation. Materials frequently used as a support are porous solids with high total surface areas (external and internal) which can provide high concentrations of active sites per unit weight of catalyst. The catalyst support may enhance the function of the catalyst agent. A supported metal catalyst is a supported catalyst in which the catalyst agent is a metal.

A catalyst that is not supported on a catalyst support material is an unsupported catalyst. An unsupported catalyst may be platinum black or a Raney catalyst. The term "Raney catalyst" as used herein refers to catalysts that have a high surface area due to selectively leaching an alloy containing the active metal(s) and a leachable metal (usually aluminum). The term Raney catalyst is not meant to denote any particular source of the material. Raney catalysts have high activity due to the higher specific area and allow the use of lower temperatures in hydrogenation reactions. The active metals of Raney catalysts include nickel, copper, cobalt, iron, rhodium, ruthenium, rhenium, osmium, iridium, platinum, palladium; compounds thereof; and combinations thereof.

Promoter metals may also be added to the base Raney metals to affect selectivity and/or activity of the Raney catalyst. Promoter metals for Raney catalysts may be selected from transition metals from Groups IIIA through VIIIA, IB and IIB of the Periodic Table of the Elements. Examples of promoter metals include chromium, molybdenum, platinum, rhodium, ruthenium, osmium, and palladium, typically at about 2% by weight of the total metal.

The catalyst support useful herein can be any solid, inert substance including, but not limited to, oxides such as silica, alumina and titania; barium sulfate; calcium carbonate; and carbons. The catalyst support can be in the form of powder, granules, pellets, or the like.

A preferred support material of the invention is selected from the group consisting of carbon, alumina, silica, silica-alumina, silica-titania, titania, titania-alumina, barium sulfate, calcium carbonate, strontium carbonate, compounds thereof and combinations thereof. Supported metal catalysts can also have supporting materials made from one or more compounds. More preferred supports are carbon, alumina, titania and silica. Further preferred supports are carbons with a surface area greater than 100 $m^2/g$. A further preferred support is carbon with a surface area greater than 200 $m^2/g$. Preferably, the carbon has an ash content that is less than 5% by weight of the catalyst support; the ash content is the inorganic residue (expressed as a percentage of the original weight of the carbon) which remains after incineration of the carbon.

Commercially available carbons which may be used in this invention include those sold under the following trademarks: Barneby & Sutcliffe™, Darco™, Nuchar™, Columbia JXN™, Columbia LCK™, Calgon PCB™, Calgon BPL™, Westvaco™, Norit™ and Barnaby Cheny NB™. The carbon can also be commercially available carbon such as Calsicat C, Sibunit C, or Calgon C (commercially available under the registered trademark Centaur(R)).

In the processes of the invention, the preferred content of the metal catalyst in the supported catalyst is from about 0.1% to about 20% of the supported catalyst based on metal catalyst weight plus the support weight. A more preferred metal catalyst content range is from about 1% to about 10% of the supported catalyst. A further preferred metal catalyst content range is from about 3% to about 7% of the supported catalyst.

Combinations of catalyst and support system may include any one of the metals referred to herein with any of the supports referred to herein. Preferred combinations of catalyst and support include palladium on carbon, palladium on silica, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina, ruthenium on silica and combinations thereof.

Further preferred combinations of catalyst and support include palladium on carbon, palladium on alumina, palladium on titania, ruthenium on carbon, ruthenium on alumina, rhodium on carbon, rhodium on alumina, platinum on carbon, platinum on alumina, iridium on silica, iridium on carbon, iridium on alumina and combinations thereof.

The levulinic acid useful in the processes of the invention may be obtained using traditional chemical routes or obtained from biobased, renewable cellulosic feedstocks. Utilization of bio-derived levulinic acid is likely to reduce the cost of manufacture of the compounds herein relative to conventional methods.

The compounds produced by the processes of the current invention display properties that are useful in diverse applications. N-alkyl pyrrolidones with alkyl chains up to about 8 carbons function as aprotic chemical solvents with a lower toxicity profile than other solvents. The carbon chains of N-lower pyrrolidones are not long enough to allow micelle formation in water; thus these compounds do not exhibit significant surfactant properties. N-alkyl pyrrolidones with alkyl groups of about $C_8$ to $C_{14}$ exhibit surfactant properties, and pyrrolidones with longer N-alkyl chains act as complexing agents. The surface active properties of alkyl pyrrolidones, such as solubility, wetting, viscosity building, emulsifying and complexing are described in U.S. Pat. No. 5,294,644. N-alkyl pyrrolidones can also be used for concentrating colloidal particles. Due to their solvent, surfactant and complexing properties, pyrrolidones are very useful in the manufacture of pharmaceuticals, personal care products, and industrial, agricultural and household chemicals and products.

The pyrrolidones produced by the processes of the invention are useful in preparing pharmaceutical products for use on humans, animals, reptiles, and fish. The pyrrolidones disclosed herein are particularly useful in topical formulations, such as ointments, creams, lotions, pastes, gels, sprays, aerosols, lotions, shampoos, foams, creams, gels, ointments, salves, milks, sticks, sprays, balms, emulsions, powders, solid or liquid soaps, or oils. Pyrrolidones, such as 5-methyl-2-pyrrolidones, can be used to enhance the transdermal penetration of active components into human or animal tissues and systems. Pyrrolidones can also act as solubilizers to enhance the solubility of a therapeutic agent in the carrier system.

The pyrrolidones produced by the processes of the invention may also be incorporated into matrix systems, such as patches, for the transdermal administration of, for example, an antimicrobial, a hormone, or an anti-inflammatory. The methods of preparation of pharmaceutical compositions as are commonly practiced in the pharmaceutical industry are useful with the processes of the invention. For discussion of such methods, see, for example, Remington's Pharmaceutical Sciences (A R Gennaro, ed., $20^{th}$ Edition, 2000, Williams & Wilkins, Pa.) incorporated herein by reference.

The pyrrolidones made by the processes of the invention may be used as solvents or surfactants in liquid, gel or aerosol cleaning compositions for cleaning a wide range of surfaces, including textiles, such as clothing, fabrics and carpets, and hard surfaces, such as glass, metal, ceramics, porcelain, synthetic plastics and vitreous enamel. The pyrrolidones may also be used in formulations for disinfecting hard surfaces, such as in the household, or in institutional or hospital environments, or the surface of skin, or fabric surfaces, or in the food preparation, restaurant or hotel industries. In addition, cleaning compositions are useful for the removal of industrial soils, such as dirt, grease, oil, ink and the like. The pyrrolidones may also be used as solvents in compositions for cleaning, solvating, and/or removing plastic resins or polymers from manufactured articles or manufacturing equipment.

In addition to pyrrolidones, other components may be included in cleaning compositions. These additional components include nonionic surfactants, anionic surfactants, cationic surfactants, amphoteric surfactants and solvents. Illustrative nonionic surfactants are alkyl polyglycosides, such as Glucopon (Henkel Corporation), ethylene oxide and mixed ethylene oxide/propylene oxide adducts of alkylphenols, the ethylene oxide and mixed ethylene oxide/propylene oxide adducts of long chain alcohols or of fatty acids, mixed ethylene oxide/propylene oxide block copolymers, esters of fatty acids and hydrophilic alcohols, such as sorbitan monooleate, alkanolamides, and the like.

Illustrative anionic surfactants are the soaps, higher alkylbenzene sulfonates containing from 9 to 16 carbons in the higher alkyl group in a straight or branched chain, $C_8$–$C_{15}$ alkyl toluene sulfonates, $C_8$–$C_{15}$ alkyl phenol sulfonates, olefin sulfonates, paraffin sulfonates, alcohol and alcoholether sulfates, phosphate esters, and the like.

Illustrative cationic surfactants include amines, amine oxides, alkylamine ethoxylates, ethylenediamine alkoxylates such as the Tetronic® series from BASF Corporation, quaternary ammonium salts, and the like.

Illustrative amphoteric surfactants are those which have both acidic and basic groups in their structure, such as amino and carboxyl radicals or amino and sulfonic radicals, or amine oxides and the like. Suitable amphoteric surfactants include betaines, sulfobetaines, imidazolines, and the like.

Illustrative solvents include glycols, glycol ethers, aliphatic alcohols, alkanolamines, pyrrolidones and water.

Such surfactants and solvents are described, for example, in McCutcheon's (2002), Volume 1 (Emulsifiers and Detergents) and Volume 2 (Functional Materials), The Manufacturing Confectioner Publishing Co., Glen Rock, N.J.

Cleaning compositions may also include additional components, such as chelating agents, corrosion inhibitors, antimicrobial compounds, buffering and pH adjusting agents, fragrances or perfumes, dyes, enzymes and bleaching agents.

N-alkyl-2-pyrrolidones are useful in cleaning and stripping formulations which are used to remove (or strip) a photoresist film (or other similar organic polymeric material film) or layer from a substrate, or to remove or clean various types of plasma-etch residues from a substrate. N-alkyl-2-pyrrolidones are also useful as surfactants in cleaning formulations for removing solder pastes from printing applicators and circuit assemblies.

N-alkyl-2-pyrrolidones, such as 5-methyl-N-octyl-2-pyrrolidone and 5-methyl-N-dodecyl-2-pyrrolidone, may be included as components in ink jet inks in order to improve resistance to highlighter smear when printed into an image, lead to an even print (minimize the degree of banding) and impart an improved waterfast resistance and/or a better dry or wet rub property. 2-Pyrrolidones, such as 5-methyl-N-cyclohexyl-2-pyrrolidone or 5-methyl-N-methyl-2-pyrrolidone, may also be used as a solvent in the preparation of hot melt or phase change inks for color printing.

The pyrrolidones made by the processes of the invention can also be utilized in the manufacture of agrochemicals, including but not limited to herbicides, insecticides, fungicides, bactericides, nematicides, algicides, mulluscicides, virucides, compounds inducing resistance to plants, repellants of birds, animals and insects, and plant growth regulators, or mixtures thereof. The method of manufacture comprises contacting an agrochemically effective agent as known to persons skilled in the art with at least one of the pyrrolidones produced by any of the methods of the invention. The agrochemical composition can optionally comprise additional auxilary components as are commonly used in the agrochemical industry.

Pyrrolidones, such as 5-methyl-N-methylpyrrolidone and 5-methyl-N-cyclohexyl pyrrolidone, can be used as water insoluble polar co-solvents to solubilize water insoluble pesticides and other agrochemicals and increase the effective amount of active ingredient. N-alkyl pyrrolidones, preferably N—$C_{3-15}$ alkyl pyrrolidones, in particular 5-methyl-N-octyl pyrrolidone and 5-methyl-N-dodecylpyrrolidone, can be used as nonionic surfactants that aid as emulsifiers. Plant growth regulators are used to improve the economic yield of agricultural plants. 5-Methyl-N-octyl pyrrolidone and 5-methyl-N-dodecyl pyrrolidone can be utilized as solvents in emulsions containing plant growth regulators.

In addition, pyrrolidones can be utilized in liquid or aerosol formulations for dermal application of insect repellants by humans; examples include mosquito and tick repellants. Manufacture of such insect repellants comprises contacting an effective amount of at least one insect repelling agent with at least one product produced using at least one process of the invention.

Pyrrolidones, such as 5-methyl-N-methyl-2-pyrrolidone, can also be used in antimicrobial formulations for the preservation of animal silage.

5-Methyl-N-alkyl-2-pyrrolidones can also be used as part of a more environmentally-conscious method for dry-cleaning clothing that includes a surfactant and densified carbon dioxide in place of traditional solvents.

In addition, 5-methyl-2-pyrrolidones can be used as components in a protective composition for use on painted surfaces, such as cars. The pyrrolidones function to wet the surface and promote spreadibility of the protectant.

Different plastic materials are often not miscible, resulting in products that exhibit insufficient mechanical properties. Monomeric and polymeric 5-methyl-pyrrolidone-containing compounds can be used as compatibilizers for plastic compositions; the compatibilizers attach themselves to the interface between the polymers involved, or penetrate into the polymers, thereby improving the adhesion between the polymers and enhancing mechanical properties.

5-Methyl-N-pyrrolidones can also be used as compatibilizers in the refrigeration and air conditioning industries. Transitioning from chlorofluorocarbon to hydrofluorocarbon refrigerants has necessitated the use of a new class of lubricants due to immiscibility with conventional lubricants such as mineral oil, poly α-olefin and alkylbenzene. However the new class of lubricants is expensive and also very hygroscopic. Absorption of water leads to acid formation and corrosion of the refrigeration system, as well as the formation of sludges. The lack of solubility of the hydrofluorocarbons in the conventional lubricants results in a highly viscous lubricant in the non-compressor zones, and results in insufficient lubricant return to the compressor. This can eventually result in a number of problems, including the compressor overheating and seizing and insufficient heat transfer in the refrigeration system. Compatibilizers solubilize the polar halogenated hydrocarbon refrigerant and the conventional non-polar lubricant in the non-compressor zones, which results in efficient return of lubricant to the compressor zone. Compatibilizers may include the 5-methyl-N-alkyl- and 5-methyl-N-cycloalkyl-2-pyrrolidones.

Pyrrolidones can also be used as fuel and lubricant additives. For example, N-alkyl-2-pyrrolidones can be used as detergents and dispersants in fuel additive compositions to keep valves, carburetors and injection systems clean, thereby improving the combustion characteristics and reducing deposits, thus reducing air polluting emissions. In addition, 5-methyl-N-methyl-2-pyrrolidone can be used to remove unsaturated hydrocarbons from raw lube distillates or deasphalted residual lube stocks to produce solvent-refined base oils as lubricants.

Methods for the preparation of cleaning, stripping, agrochemical and plastic formulations are well known to persons skilled in the art. Similarly, methods for the preparation of insect repellants, ink jet inks, protective formulations for paint, fuel additives and lubricants, refrigeration and air conditioning lubricants, and for dry cleaning are well known in the art. Pyrrolidones can act as solvents, surfactants, dispersants, detergents, emulsifiers, viscosity builders and complexing agents in these formulations. Appropriate pyrrolidones are selected based on standard screening procedures for product performance. Additional components, such as pharmaceutical or agrochemical active agents or colorants, may be added to specific formulations as the main functional component; the nature of the functional component or components would be determined by the specific use. Auxiliary components, which enhance or are critical to the efficacy of the formulation, may also be added. Auxiliary components may include solvents or cosolvents, thickeners, antioxidants, spreading agents, preservatives, adhesives, emulsifiers, defoamers, humectants, dispersants, surfactants, suitable carriers, matrix systems, delivery vehicles, fragrances, salts, esters, amides, alcohols, ethers, ketones, acids, bases, alkanes, silicone, evaporation modifiers, paraffins, aliphatic or aromatic hydrocarbons, chelating agents, gases for aerosols, propellants or for dry cleaning, oils and water. Appropriate auxiliary components for the uses described herein are known to persons skilled in the art.

The following examples are illustrative of the invention. Examples 1 to 56 are actual examples; Examples 57 to 62 are prophetic.

EXAMPLES

The following abbreviations are used:

| | |
|---|---|
| ESCAT-XXX: | Series of catalysts provided by Engelhard Corp. (Iselin, NJ) |
| JM-AXXXX, JM-XXXX: | Series of catalysts from Johnson Matthey, Inc. (W. Deptford, NJ) |
| Calsicat Carbon: | Catalyst support from Engelhard Corp. |
| Sibunit Carbon: | Catalyst support from Inst. of Technical Carbon, Omsk, Russia |
| Calgon Carbon: | Catalyst support from Calgon Carbon Corp. under the brand name of Centaur(R) (Pittsburgh, PA) |
| ST-XXXX-SA: | Series of catalysts from Strem Chemicals (Newburyport, MA) |
| SCCM: | Standard cubic centimeters per minute |
| GC: | Gas chromatography |
| GC-MS: | Gas chromatography-mass spectrometry |

For catalyst preparation a commercially available support such as carbon, alumina, silica, silica-alumina or titania was impregnated by incipient wetness with a metal salt. The catalyst precursors used were $NiCl_2 \cdot 6H_2O$ (Alfa Chemical Co., Ward Hill, Mass.), $Re_2O_7$ (Alfa Chemical Co.), $PdCl_2$ (Alfa Chemical Co.), $IrCl_3 \cdot 3H_2O$ (Alfa Chemical Co.), $RuCl_3 \cdot xH_2O$ (Aldrich Chemical Co., Milwaukee, Wis.), $H_2PtCl_6$ (Johnson Matthey, Inc.), and $RhCl_3 \cdot xH_2O$ (Alfa Chemical Co.). The samples were dried and reduced at 300–450° C. under $H_2$ for 2 hours.

The carbon used was commercially available as Calsicat Carbon, Sibunit Carbon, or Calgon Carbon (commercially available under the registered trademark Centaur(®). Calsicat Carbon is lot S-96–140 from Engelhard Corp. Sibunit Carbon is Sibunit-2 from Institute of Technical Carbon, 5th Kordnaya, Omsk 64418, Russia. Calgon Carbon is PCB Carbon from Calgon Corp. (commercially available under the registered trademark of Centaur(®). Raney catalysts are available from W. R. Grace & Co. (Columbia, Md.), and pentenenitrile, benzonitrile, adiponitrile, propionitrile, dioxane and ethyl levulinate are available from Fisher Scientific (Chicago, Ill.).

Catalyst Preparation: 5% Pt on Acid Washed Calsicat Carbon

In a 150 ml beaker, a solution was made up of 4.5 ml 0.3 M $H_2PtCl_6$ with 4.0 ml deionized $H_2O$. To the beaker were added 4.75 g Calsicat Acid Washed Carbon (12×20 mesh, dried at 120° C. overnight). The slurry was allowed to stand at room temperature for 1 hr with occasional stirring, followed by drying at 120° C. overnight with frequent stirring (until free flowing).

In an alumina boat, in a quartz lined tube furnace, the catalyst was purged with 500 SCCM $N_2$ at room temperature for 15 min and then with 100 SCCM He at room temperature for 15 min. The catalyst was heated to 150° C. and held at 150° C. under He for 1 hr. At this point, 100 SCCM $H_2$ were added and the sample was held at 150° C. under He and $H_2$ for 1 hr. The temperature was increased to 300° C. and the catalyst was reduced at 300° C. under He-$H_2$ for 8 hrs. The $H_2$ was stopped, the sample was held at 300° C. under He for 30 min and then cooled to room temperature in flowing He. The catalyst was finally passivated in 1.5% $O_2$ in $N_2$ at 500 SCCM for 1 hr at room temperature and weighed 4.93 g when unloaded.

Additional catalysts used in the present invention were prepared following a similar procedure.

Batch Reduction of Ethyl Levulinate to 5-Methyl-N-(Methyl Aryl)-2-Pyrrolidone and 5-Methyl-N-(Methyl Cycloalkyl)-2-Pyrrolidone To a 5 ml pressure vessel was added 50 gm of catalyst, and 1 gm of a solution containing 30 wt % ethyl levulinate, 22% aryl cyano compound and 48% dioxane. The vessel was sealed, charged with 5.52 MPa hydrogen and heated to 150° C. for 4 hours. The pressure was maintained at 5.52 MPa during the course of the reaction. At the end of the reaction, the vessel was rapidly cooled in ice, vented and an internal GC standard of methoxyethylether was added. The solution was separated by pipette from the catalyst and analyzed by GC-MS using an HP 6890 (Agilent; Palo Alto, Calif.) equipped with a FFAP 7717 (30 meter) column. The results set forth in the tables below are based on area %.

The examples described below were performed according to a similar procedure under the conditions indicated.

Examples 1–12

Preparation of Hexane-1,6-(5-Methyl-2-Pyrrolidone) (HDMP) by Batch Reduction of Ethyl Levulinate (EL) Using Adiponitrile (ADPN) as the Alkyl Cyano Compound The reactions were carried out for 4 hours at a temperature and pressure of 150° C. and 5.52 MPa, respectively. The feedstock was ethyl levulinate/adiponitrile/dioxane at a ratio (wt. %) of 40/15/45. The results are set forth in the following table.

| Ex. No. | Catalyst/Support[a] | EL Conversion (%) | HDMP (dimer) Selectivity (%) |
|---|---|---|---|
| 1 | 5% Pd/C (ESCAT-142) | 38.3 | 1.8 |
| 2 | 5% Pt/C (ESCAT-248) | 48.0 | 3.2 |
| 3 | 5% Rh/C (JM-11761) | 54.1 | 3.1 |
| 4 | 5% Ru/C (ESCAT-440) | 92.2 | 21.7 |
| 5 | 5% Re/C (Fisher) | 8.8 | 0.0 |
| 6 | 5% Ir/Calsicat C | 84.9 | 10.5 |
| 7 | 5% Pd/$Al_2O_3$ (ESCAT-124) | 53.8 | 9.1 |
| 8 | 5% Pt/$Al_2O_3$ (ESCAT-294) | 67.4 | 12.9 |
| 9 | 5% Rh/$Al_2O_3$ (Fisher) | 62.7 | 4.3 |
| 10 | 5% Ru/$Al_2O_3$ (ESCAT-44) | 85.5 | 20.1 |
| 11 | 5% Re/$Al_2O_3$ | 6.1 | 0.0 |
| 12 | 5% Ir/$Al_2O_3$ | 84.1 | 19.0 |

[a]Source for commercially available catalyst/support is in parentheses.

Examples 13–30

Preparation of 5-Methyl-N-Propyl-2-Pyrrolidone (PrMP) and 5-Methyl-2-Pyrrolidone (MP) by Batch Reduction of Ethyl Levulinate (EL) Using Propionitrile (PN) as the Alkyl Cyano Compound The reactions were carried out for 4 hours at a temperature and pressure of 150° C. and 5.52 MPa, respectively. The feedstock was ethyl levulinate/propionitrile/dioxane at a ratio (wt. %) of 30/15/55. The results are set forth in the following table.

| Ex. No. | Catalyst/Support[a] | EL Conversion (%) | PrMP Selectivity (%) | MP Selectivity (%) |
|---|---|---|---|---|
| 13 | 5% Pd/C (ESCAT-142) | 59.6 | 55.6 | 30.3 |
| 14 | 5% Pt/C (ESCAT-248) | 51.6 | 43.3 | 32.9 |
| 15 | 5% Ru/C (ST-141060-SA) | 84.9 | 30.6 | 32.6 |
| 16 | 5% Rh/C (JM-11761) | 73.3 | 40.9 | 53.4 |
| 17 | 5% Re/C (Fisher) | 3.1 | 42.6 | 27.4 |
| 18 | 5% Ir/Calsicat C | 93.9 | 48.0 | 19.6 |
| 19 | 5% Pd/$Al_2O_3$ | 92.9 | 42.5 | 51.2 |
| 20 | 5% Pt/$Al_2O_3$ (ESCAT-294) | 77.9 | 47.4 | 49.2 |
| 21 | 5% Ru/$Al_2O_3$ (ESCAT-44) | 88.5 | 58.0 | 30.4 |
| 22 | 5% Rh/$Al_2O_3$ (Fisher) | 71.6 | 35.1 | 62.4 |
| 23 | 5% Re/$Al_2O_3$ | 1.6 | 16.7 | 21.6 |
| 24 | 5% Ir/$Al_2O_3$ | 95.7 | 54.1 | 29.6 |
| 25 | 5% Pd/$SiO_2$ | 89.8 | 50.5 | 40.1 |
| 26 | 5% Pt/$SiO_2$ | 79.2 | 40.2 | 53.0 |
| 27 | 5% Ru/$SiO_2$ | 92.2 | 51.0 | 27.0 |
| 28 | 5% Rh/$SiO_2$ | 82.9 | 41.7 | 50.3 |
| 29 | 5% Re/$SiO_2$ | 3.7 | 42.6 | 11.7 |
| 30 | 5% Ir/$SiO_2$ | 96.9 | 64.0 | 25.2 |

[a]Source for commercially available catalyst/support is in parentheses.

Examples 31–48

Preparation of 5-Methyl-N-(Methyl Phenyl)-2-Pyrrolidone (PMP) and 5-Methyl-N-(Methyl Cyclohexyl)-2-Pyrrolidone (CHMMP) by Batch Reduction of Ethyl Levulinate (EL) Using Benzonitrile (BN) as the Aryl Cyano Compound The reactions were carried out for 4 hours at a temperature and pressure of 150° C. and 5.52 MPa, respectively. The feedstock was ethyl levulinate/benzonitrile/dioxane at a ratio (wt. %) of 30/22/48. The results are set forth in the following table.

| Ex. No. | Catalyst/Support[a] | EL Conversion (%) | PMP Selectivity (%) | CHMMP Selectivity (%) |
|---|---|---|---|---|
| 31 | 5% Pd/C (ESCAT-142) | 99.8 | 7.2 | 3.2 |
| 32 | 5% Pt/C (ESCAT-248) | 89.6 | 55.7 | 0.1 |
| 33 | 5% Ru/C (ST-141060-SA) | 97.9 | 12.0 | 7.3 |
| 34 | 5% Rh/C (JM-11761) | 99.8 | 43.1 | 6.7 |
| 35 | 5% Re/C (Fisher) | 3.3 | 36.6 | 3.0 |
| 36 | 5% Ir/Calsicat C | 96.9 | 61.1 | 1.5 |
| 37 | 5% Pd/$Al_2O_3$ (JM-A22117-5) | 99.9 | 20.7 | 0.8 |
| 38 | 5% Pt/$Al_2O_3$ (ESCAT-294) | 93.8 | 59.6 | 0.4 |
| 39 | 5% Ru/$Al_2O_3$ (ESCAT-44) | 92.0 | 18.2 | 45.4 |
| 40 | 5% Rh/$Al_2O_3$ (Fisher) | 70.2 | 48.9 | 0.9 |
| 41 | 5% Re/$Al_2O_3$ | 1.2 | 19.1 | 3.3 |
| 42 | 5% Ir/$Al_2O_3$ | 95.8 | 66.3 | 0.7 |
| 43 | 5% Pd/$SiO_2$ | 99.9 | 35.5 | 1.1 |
| 44 | 5% Pt/$SiO_2$ | 95.9 | 64.3 | 0.6 |
| 45 | 5% Ru/$SiO_2$ | 99.1 | 10.1 | 5.6 |
| 46 | 5% Rh/$SiO_2$ | 99.6 | 36.0 | 8.4 |
| 47 | 5% Re/$SiO_2$ | 1.8 | 23.2 | 5.8 |
| 48 | 5% Ir/$SiO_2$ | 97.9 | 68.6 | 3.1 |

[a]Source for commercially available catalyst/support is in parentheses.

Examples 49–56

Preparation of 5-Methyl-N-Pentyl-2-Pyrrolidone (PeMP) by Batch Reduction of Ethyl Levulinate (EL) Using 3-Pentenenitrile (3PN) as the Alkyl Cyano Compound The reactions were carried out at 150° C. The results are set forth in the following table. Abbreviation: Con, Conversion; Sel, Selectivity.

| Ex. No. | Catalyst/Support[a] | Time (hrs) | $H_2$ Pressure (MPa) | Feedstock | Feedstock Ratio (wt %) | EL Con (%) | PeMP Sel (%) |
|---|---|---|---|---|---|---|---|
| 49 | 5% Rh/Sibunit C | 4 | 5.52 | EL/3PN/Dioxane | 35/20/45 | 73.2 | 65.9 |
| 50 | 5% Rh/Calsicat C | 4 | 5.52 | EL/3PN/Dioxane | 35/20/45 | 81.9 | 57.4 |

-continued

| Ex. No. | Catalyst/ Support[a] | Time (hrs) | H$_2$ Pressure (MPa) | Feedstock | Feedstock Ratio (wt %) | EL Con (%) | PeMP Sel (%) |
|---|---|---|---|---|---|---|---|
| 51 | 5% Rh/Calgon C | 4 | 5.52 | EL/3PN/Dioxane | 35/20/45 | 75.4 | 59.8 |
| 52 | 5% Rh/Al$_2$O$_3$ | 4 | 5.52 | EL/3PN/Dioxane | 35/20/45 | 77.9 | 61.0 |
| 53 | 5% Rh/SiO$_2$ | 4 | 5.52 | EL/3PN/Dioxane | 35/20/45 | 80.6 | 67.4 |
| 54 | 5% Rh/C (JM-11761) | 12 | 6.90 | EL/3PN | 64/36 | 91.7 | 20.2 |
| 55 | 5% Pd/C (ESCAT-142) | 12 | 6.90 | EL/3PN | 64/36 | 11.6 | 62.9 |
| 56 | 5% Ru/C (ST-141060-SA) | 12 | 6.90 | EL/3PN | 64/36 | 88.4 | 68.1 |

[a]Source for commercially available catalyst/support is in parentheses.

Example 57

Pharmaceutical Formulations

A) Topical Formulation:

| | |
|---|---|
| Solubilizer (diethylene glycol monoethyl ether) | 2% to 50% |
| Skin permeation enhancer (N-hydroxyethyl-2-pyrrolidone) | 2% to 50% |
| Emulsifier | 2% to 20% |
| Emollient (propylene glycol) | 2% to 20% |
| Preservative | 0.01 to 0.2% |
| Active agent | 0 to 25% |
| Carrier | Balance |

B) Cream:

Phase 1:

| | |
|---|---|
| Polyethylene glycol and ethylene glycol palmitostearate | 5% |
| Caprilic/capric triglycerides | 5% |
| Oleoyl macrogolglycerides (Labrafil M 1944CS) | 4% |
| Cetyl alcohol | 5.5% |
| PPG-2 myristyl ether propionate (Crodamol PMP) | 6% |
| 5-methyl-N-hydroxyethyl-2-pyrrolidone | 2% |

Phase 2:

| | |
|---|---|
| Xanthan gum | 0.3% |
| Purified water | 55% |

Phase 3:

| | |
|---|---|
| Propylene glycol | 1% |
| Methylparaben | 0.18% |
| Propylparaben | 0.02% |

Phase 4:

| | |
|---|---|
| Naftifine hydrochloride (antifungal) | 1% |
| Diethylene glycol monoethyl ether (Transcutol) | 15% |

Procedure:

Xanthan gum is dispersed in water and allowed to stand. Phase 1 components and phase 2 components are separately heated to 75° C.; phase 1 is mixed into phase 2 under high speed agitation. The temperature is maintained at 75° C. while stirring for 10 min. The mixture is then slowly cooled while stirring at low speed. At 40° C., phase 3 is added. Naftifine is then mixed well into the Transcutol, and the mixture is added to the cream, mixed well and the cream is cooled to room temperature.

C) Transdermal Patch Formulation:

| | |
|---|---|
| Ketoprofen | 0.3% |
| Polysorbate 80 | 0.5% |
| 5-Methyl-N-methyl-2-pyrrolidone | 1% |
| 5-Methyl-N-ethyl-2-pyrrolidone | 2% |
| PEG 400 | 10% |
| CMC-Na | 4% |
| Na-polyacrylate | 5.5% |
| Sanwet 1M-1000PS | 0.5% |
| Polyvinyl alcohol | 1% |
| PVP/VA copolymer | 3% |

Example 58

Cleaning Compositions

A) Grease Removal Formulation:

| | |
|---|---|
| Water | 89% |
| Potassium carbonate | 1% |
| Potassium bicarbonate | 5% |
| 5-Methyl-N-octyl-2-pyrrolidone | 2.5% |
| Deriphatec 151-C (Henkel Corp.) | 2.5% |

B) Oil-in-Water Emulsion in Aerosol Form:

| | |
|---|---|
| Crillet 45 (Croda) | 3.30% |
| Monamulse DL 1273 (Mona Industries, Inc.) | 3.30% |
| 5-Methyl-N-dodecyl-2-pyrrolidone | 5.50% |
| Denatured absolute ethanol 100 AG/F3 (CSR Ltd.) | 15.40% |
| Norpar 15 (Exxon) | 5.50% |
| Deionized water | 44.10% |
| Butane | 16.95% |
| Propane | 5.95% |

C) All-Purpose Liquid Cleaning Composition:

| | |
|---|---|
| Neodol 91-8 (Shell) | 3.5% |
| Linear alkyl (C9–13) benzene sulfonate, Mg salt | 10.5% |
| Propylene glycol mono-t-butyl ether | 4.0% |
| Coco fatty acid | 1.4% |
| 5-Methyl-N-decyl-2-pyrrolidone | 1.0% |
| Magnesium sulfate heptahydrate | 5.0% |
| Water | 74.6 |

D) Shower-Rinsing Composition:

| | |
|---|---|
| Glucopon 225 (Henkel Corp.) | 2.0% |
| Isopropyl alcohol | 2.2% |
| Sequestrene 40 (45%, Ciba) | 1.0% |
| Fragrance | 0.02% |

| | |
|---|---|
| Barquat 4250Z (50%, Lonza) | 0.2% |
| 5-Methyl-N-octyl-2-pyrrolidone | 1.0% |
| Water | 93.58% |
| E) Dishwashing Composition: | |
| Ethanol (95%) | 8.6% |
| Alfonic 1412-A [Ethylene oxide sulfate (59.3%)] | 22.5% |
| Alfonic 1412-10 | 1.1% |
| Sodium chloride | 0.9% |
| 5-Methyl-N-decyl-2-pyrrolidone | 7.5% |
| Water | 59.4% |
| F) Aqueous Antimicrobial Cleaning Composition: | |
| Adipic acid | 0.40% |
| Dacpon 27-23 AL (Condea; $C_{12-14}$ sodium alkyl sulfate, 28% active) | 0.15% |
| Isopropyl alcohol | 1.8% |
| Dowanol PnB (Dow; propylene glycol mono-N-butyl ether) | 0.30% |
| 5-Methyl-N-octyl-2-pyrrolidone | 0.4% |
| Sodium hydroxide | 0.05% |
| Water | 96.9% |

An antimicrobial wipe can be made by impregnating a substrate with the above composition; the substrate can be spunlace comprising viscose/polyester at a ratio of 70:30 with a specific weight of 50 grams/m². The composition to substrate ratio is about 2.6:1.

| | |
|---|---|
| G) Disinfectant: | |
| Benzalkonium chloride | 5% |
| Sodium carbonate | 2% |
| Sodium citrate | 1.5% |
| Nonoxynol 10 | 2.5% |
| 5-Methyl-N-octyl-2-pyrrolidone | 5% |
| Water | 84% |
| H) Anti-Parasitidal Agent (for dermal application to animals): | |
| Antiparasital agent | 1 to 20% |
| 5-Methyl-N-isopropyl-2-pyrrolidone | 30% |
| Benzyl alcohol (preservative) | 3% |
| Thickener | 0.025–10% |
| Colorant | 0.025–10% |
| Emulsifier | 0.025–10% |
| Water | Balance |

Example 59

Stripping/Cleaning Formulation

| | |
|---|---|
| 5-Methyl-N-methyl-2-pyrrolidone | 30% |
| Monoethanolamine | 55% |
| Lactic acid | 5% |
| Water | 10% |

Example 60

Ink Jet Ink

| | |
|---|---|
| CAB-O-JET 300 (Active) | 4% |
| Diethylene glycol | 17.5% |
| 5-Methyl-N-octyl-2-pyrrolidone | 2.5% |
| Deionized $H_2O$ | 76% |

Example 61

Agrochemical Compositions

| | |
|---|---|
| A) Composition for the Control of Insects: | |
| Permethrin | 2% |
| 5-Methyl-N-decyl-2-pyrrolidone | 3% |
| Dimethyl dipropyl naphthalene | 7% |
| Lauryl alcohol | 5% |
| Hymal 1071 (MatsumotoYushi Seiyaky, Inc.) | 10% |
| Hytenol N-08 (Daiichi Kogyo Seiyaku, Inc.) | 2% |
| Polyoxyethylene glycol | 71% |
| B) Pesticide Formulation: | |
| 5-Methyl-N-alkyl pyrrolidone | 48% |
| Sodium dodecyl sulfate | 12% |
| Agrimer AL25 | 10% |
| Rodeo (pesticide; Monsanto) | 1% |
| Water | 29% |
| C) Emulsifiable Fungicide Formulation: | |
| Kresoxin-methyl | 0.5% |
| Propylene carbonate | 1.5% |
| Aromatic petroleum distillate 150 (Exxon) | 2.9% |
| 5-methyl-N-octyl-2-pyrrolidone | 3.8% |
| CaH/DDBSA [50% (Ca dodecylbenzene Sulfonate + Dodecylbenzene Sulfonic acid (5:1) in Exxon 150 | 1.4% |
| Water | Balance |

Example 62

Formulation for Protective Composition for Painted Automobile Surfaces

| | |
|---|---|
| Propylene glycol phenyl ether | 2.0% |
| 5-Methyl-N-octyl-2-pyrrolidone | 0.1% |
| Emulsified silicone: | 3.0% |
| a) dimethyl silicone (2.67%) | |
| b) amino-functional silicone (0.21%) | |
| c) silicone resin (0.12%) | |
| Water | 94.9% |

What is claimed is:

1. A process for preparing an ink jet composition, the process comprising the steps of:
   i) preparing 5-methyl-N-alkyl-2-pyrrolidone (VI) using a process comprising the step of contacting a levulinic acid ester (I) with an alkyl cyano compound (V) in the presence of hydrogen gas and a metal catalyst, the metal catalyst being optionally supported, and, optionally, in the presence of a solvent;

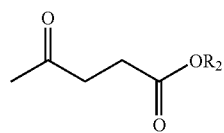
(I)

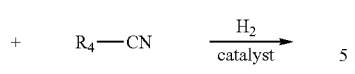
(V)

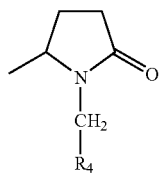
(VI)

wherein $R_2$ is hydrocarbyl or substituted hydrocarbyl, $C_1$–$C_{18}$ unsubstituted or substituted alkyl, unsubstituted or substituted alkenyl, unsubstituted or substituted alkynyl, unsubstituted or substituted cycloalkyl, unsubstituted or substituted cycloalkyl containing at least one heteroatom, unsubstituted or substituted aryl, and unsubstituted or substituted heteroaryl, and wherein $R_4$ is an alkyl group having from 1 to 30 carbons, and wherein $R_4$ may be $C_1$–$C_{30}$ unsubstituted or substituted alkyl, $C_1$–$C_{30}$ unsubstituted or substituted alkenyl, $C_1$–$C_{30}$ unsubstituted or substituted alkynyl, $C_3$–$C_{30}$ unsubstituted or substituted cycloalkyl, or $C_3$–$C_{30}$ unsubstituted or substituted cycloalkyl containing at least one heteroatom; and ii) contacting 5-methyl-N-alkyl-2-pyrrolidone (VI) with at least one colorant.

* * * * *